US010694986B2

(12) United States Patent
Hoan et al.

(10) Patent No.: US 10,694,986 B2
(45) Date of Patent: Jun. 30, 2020

(54) BRACKET FOR MOUNTING A MULTI-PORT CONTROL VALVE AND A RESERVOIR TO A SENSOR HOLDER FOR USE IN A BLOOD SAMPLING-BLOOD PRESSURE MONITORING SYSTEM

(71) Applicant: Edwards Lifesciences Corporation, Irvine, CA (US)

(72) Inventors: Andrew Nguyen Hoan, Irvine, CA (US); Mandana Farhadieh, Tustin, CA (US); Brian Patrick Murphy, Costa Mesa, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 16/131,779

(22) Filed: Sep. 14, 2018

(65) Prior Publication Data
US 2019/0125235 A1 May 2, 2019

Related U.S. Application Data

(63) Continuation of application No. 15/801,009, filed on Nov. 1, 2017.

(51) Int. Cl.
*F16M 11/00* (2006.01)
*A61B 5/15* (2006.01)
(Continued)

(52) U.S. Cl.
CPC ........ *A61B 5/150221* (2013.01); *A61B 5/021* (2013.01); *A61M 5/1413* (2013.01); *A61M 39/223* (2013.01)

(58) Field of Classification Search
CPC ... A61B 5/021; A47G 23/0291; A61M 5/1408
See application file for complete search history.

(56) References Cited

U.S. PATENT DOCUMENTS 2,954,028 A * 9/1960 Smith ................. A61M 5/1408
604/80
3,157,201 A 11/1964 Littman
(Continued)

FOREIGN PATENT DOCUMENTS

FR 2914840 A1 10/2008
WO 8500982 A1 3/1985
(Continued)

OTHER PUBLICATIONS

BIOPAC Systems, Inc., Noninvasive Blood Pressure Amplifier, Oct. 2, 2017, Inset Figure—Clamp.
(Continued)

*Primary Examiner* — Amy J. Sterling

(57) ABSTRACT

Disclosed is a multi-port control valve with multi-lumen paths diverging flow so that, the multi-port control valve fills and expels fluid at the same time through the same port for use in a blood sampling, blood pressure monitoring system that includes a sampling site, a pressure transducer, and reservoir. The multi-port control valve may include a rotatable valve member and three ports. Each of the three ports is connected to one of the sampling site, the pressure transducer, and the reservoir. In particular, the rotatable valve member is rotatable, such that, depending upon a position of the rotatable valve member, one of the three ports is blocked from fluid communication with the other two ports.

13 Claims, 9 Drawing Sheets

(51) Int. Cl.
*A61B 5/021* (2006.01)
*A61M 5/14* (2006.01)
*A61M 39/22* (2006.01)

(56) References Cited

U.S. PATENT DOCUMENTS

| | | | |
|---|---|---|---|
| 3,780,972 A * | 12/1973 | Brodersen | A62C 13/78 248/313 |
| 4,211,380 A | 7/1980 | Lillegard et al. | |
| 4,428,383 A * | 1/1984 | DeVroom | A61B 5/0215 137/883 |
| 4,858,127 A | 8/1989 | Kron et al. | |
| 4,865,583 A | 9/1989 | Tu | |
| 4,904,245 A | 2/1990 | Chen et al. | |
| 5,417,395 A | 5/1995 | Fowler et al. | |
| 5,643,218 A | 7/1997 | Lynn et al. | |
| 5,961,472 A | 10/1999 | Swendson et al. | |
| 6,105,912 A | 8/2000 | Lindsay et al. | |
| 6,156,019 A | 12/2000 | Langevin | |
| 7,240,882 B2 | 7/2007 | Degentesh et al. | |
| 7,744,573 B2 | 6/2010 | Gordon et al. | |
| 7,918,422 B2 | 4/2011 | Blankenship et al. | |
| 7,963,951 B2 | 6/2011 | Kitani et al. | |
| 8,348,844 B2 | 1/2013 | Kunjan et al. | |
| 8,382,696 B2 | 2/2013 | Beiriger et al. | |
| 8,403,874 B2 | 3/2013 | Baraldi | |
| 8,662,458 B2 | 3/2014 | Henault et al. | |
| 8,668,178 B2 * | 3/2014 | Ziaylek | F17O 13/084 224/570 |
| 8,764,668 B2 | 7/2014 | Roteliuk et al. | |
| 8,945,051 B2 | 2/2015 | Schriver et al. | |
| 8,986,262 B2 | 3/2015 | Young et al. | |
| 9,016,316 B2 | 4/2015 | Ziv et al. | |
| 9,022,981 B2 | 5/2015 | Oesterreich et al. | |
| 9,259,527 B2 | 2/2016 | Spohn et al. | |
| 9,370,324 B2 | 6/2016 | Barrett et al. | |
| 9,375,561 B2 | 6/2016 | Mansour et al. | |
| 9,566,385 B2 | 2/2017 | Franks | |
| 2007/0119508 A1 | 5/2007 | West et al. | |
| 2008/0200837 A1 | 8/2008 | Frazier et al. | |
| 2008/0302932 A1 | 12/2008 | Mosler et al. | |
| 2014/0276215 A1 | 9/2014 | Nelson et al. | |
| 2016/0144110 A1 | 5/2016 | Ueda | |
| 2016/0346472 A1 | 12/2016 | Mitchell et al. | |

FOREIGN PATENT DOCUMENTS

| | | |
|---|---|---|
| WO | 2013146752 A1 | 10/2013 |
| WO | 2016041948 A1 | 3/2016 |

OTHER PUBLICATIONS

Mark Siobal, Analysis and Monitoring of Gas Exchange, https://clinicalgate.com/analysis-and-monitoring-of-gas-exchange/, Jan. 6, 2015.

* cited by examiner

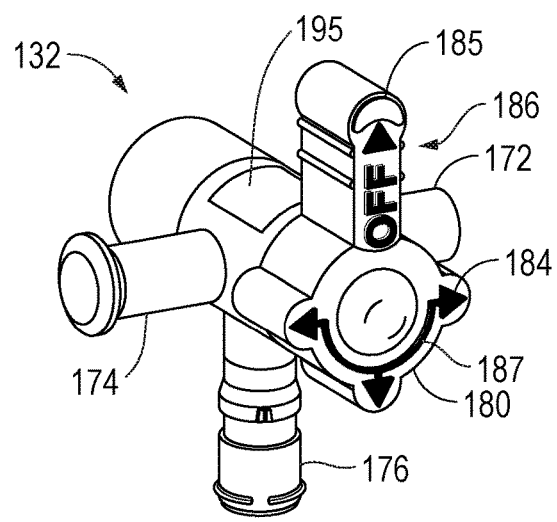
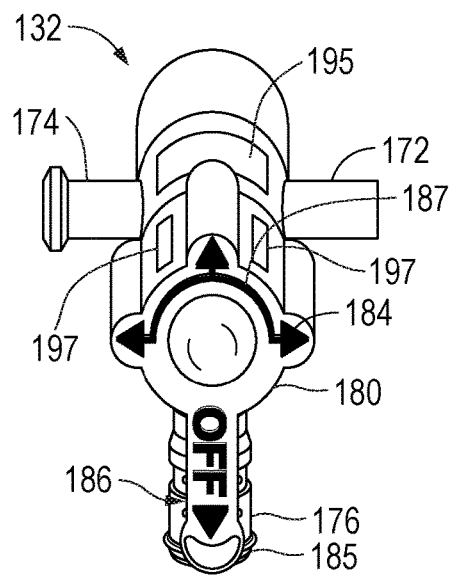
FIG. 3A                FIG. 3B
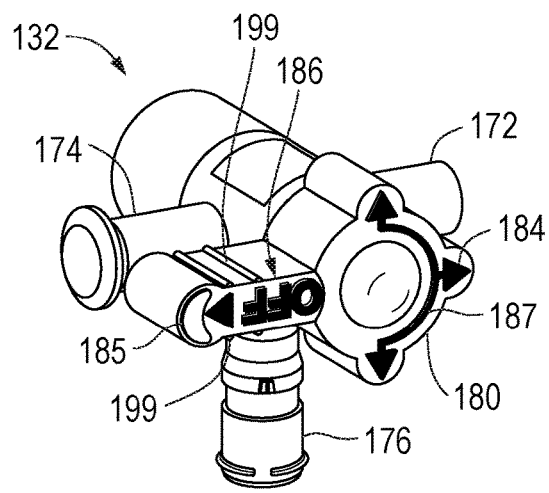
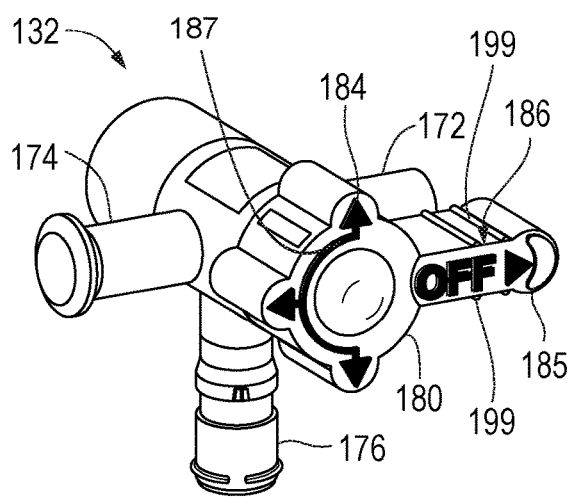
FIG. 3C                FIG. 3D

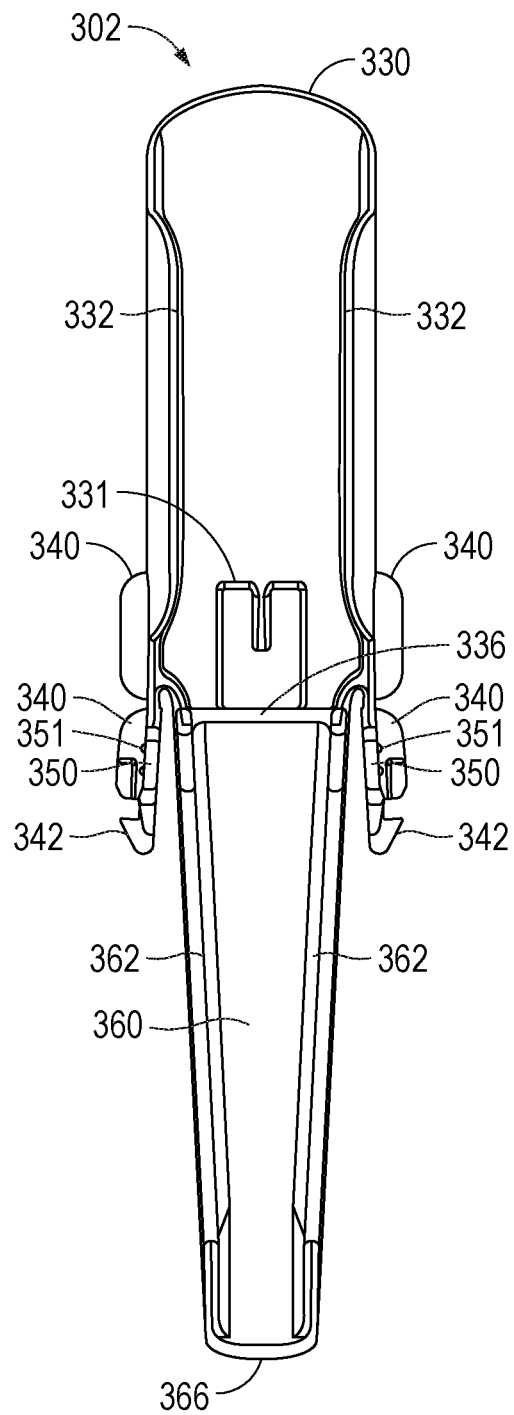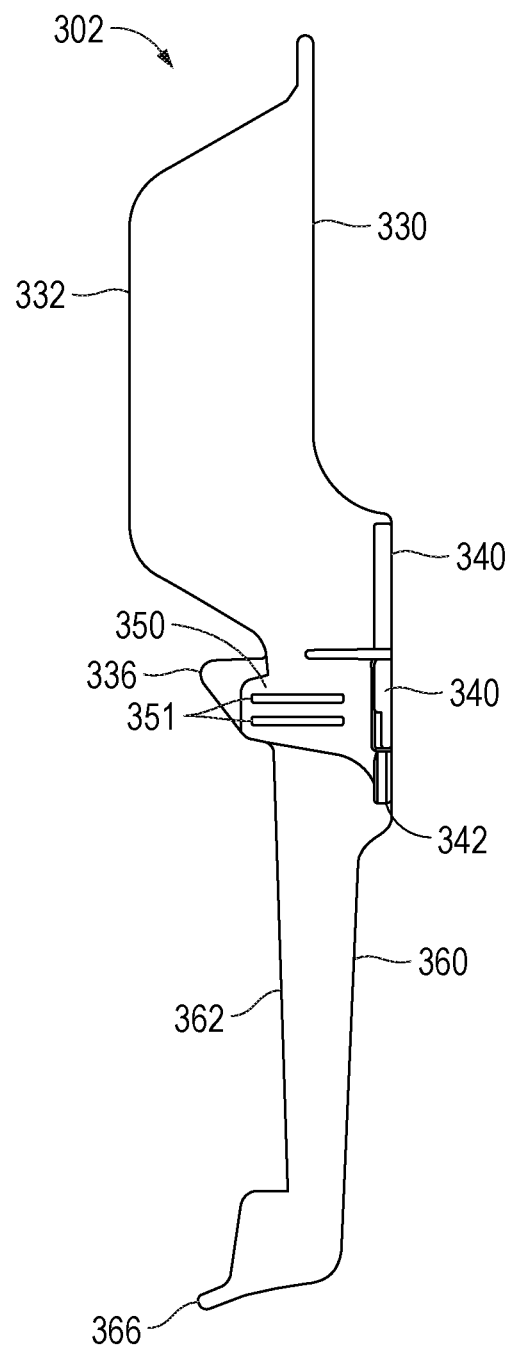
FIG. 6B
FIG. 6C

BRACKET FOR MOUNTING A MULTI-PORT CONTROL VALVE AND A RESERVOIR TO A SENSOR HOLDER FOR USE IN A BLOOD SAMPLING-BLOOD PRESSURE MONITORING SYSTEM

CROSS-REFERENCE TO RELATED APPLICATIONS

This application is a continuation application of, and claims the benefit of priority to, U.S. patent application Ser. No. 15/801,009, filed Nov. 1, 2017, the entire contents of which are incorporated herein by reference.

BACKGROUND

Field

The present invention relates to blood sampling, blood pressure measurement systems, and, in particular, to a multi-port control valve for use in a blood sampling, blood pressure measurement system.

Relevant Background

In a hospital setting there is always the need to monitor patient health through the evaluation of a blood chemistry profile. The simplest method employed in the hospital is to use a syringe carrying a sharpened cannula at one end and insert that cannula into a vein or artery to extract a blood sample from the patient. Patients that are in critical care units or the operating room sometimes require as many as twelve samples a day. Such frequent sampling injections potentially expose the patient to airborne bacteria and viruses which can enter the bloodstream through the opening made by the sharpened cannula.

One way to obtain a blood sample is to draw the blood from a catheter that is already inserted in the patient, either in a central venous line, such as one placed in the right atrium, or in an arterial line. Typically, existing access sites for arterial or venous or pressure monitoring lines are used to take periodic blood samples from the patient. Conventional mechanisms for drawing blood from the lines used for infusion or pressure monitoring utilize a plurality of stopcock mechanisms that preclude flow from the infusion fluid supply or from the pressure column drip supply, while allowing blood to flow from the patient into a collecting syringe connected to a proximal port formed in one of the stopcocks.

Earlier systems required a two-step operation where a first sample of fluid, generally about 5 ml in volume for intensive care environments was withdrawn into the sampling syringe and discarded. This first sample potentially included some of the infusion fluid and thus would be an unreliable blood chemistry measurement sample. After the initial sample had been discharged, the second sample was pure blood from the artery or vein.

In response to the drawbacks associated with earlier two-step sampling systems, closed systems were developed. Commercial closed systems such as the Venous Arterial blood Management Protection (VAMP) system feature a reservoir in the tubing line from the patient that can draw fluid past a sampling port. The clearing volume is held in the in-line reservoir, and set-aside in a syringe for re-infusion later. The sampling systems are often used in conjunction with a pressure monitor having a transducer continually or periodically sensing pressure within the sampling line except during the draw of a blood sample.

The VAMP system conveniently utilizes a reservoir with one-handed operability, and includes a line from the patient into and out of the reservoir and to a proximal source of flushing fluid and a pressure transducer. (The standard directional nomenclature is that proximal is toward the clinician, or away from the patient, and distal is toward the patient). A pressure transducer in the line proximal to the reservoir senses fluid pressure within the line and conveys the signal to a monitor. One exemplary pressure transducer is a Disposable Pressure Transducer (DPT).

When a blood sample is to be taken, the nurse or clinician withdraws an amount of fluid into the reservoir chamber and distal line sufficient to pull pure blood past one or more fluid sampling sites. After full retraction of the plunger, the stopcock valve closes off the reservoir from the patient and a sample of blood is taken at one or the other sampling sites. Subsequently, the clinician manipulates the stopcock valve so that the volume within the reservoir can be reinfused back into the patient by depressing the plunger, and the flushing drip and pressure monitoring resumes.

SUMMARY

Embodiments of the invention may relate to a multi-port control valve with multi-lumen paths diverging flow so that, the multi-port control valve fills and expels fluid at the same time through the same port for use in a blood sampling, blood pressure monitoring system that includes a sampling site, a pressure transducer, and reservoir. The multi-port control valve may include a rotatable valve member and three ports. Each of the three ports is connected to one of the sampling site, the pressure transducer, and the reservoir. In particular, the rotatable valve member is rotatable, such that, depending upon a position of the rotatable valve member, one of the three ports is blocked from fluid communication with the other two ports

BRIEF DESCRIPTION OF THE DRAWINGS

FIGS. 3A-3D are diagrams illustrating perspective views of the multi-port control valve in various modes of operation, according to embodiments of the invention.

FIGS. 6A-6C are diagrams illustrating various views of a bracket having a clip to mount the multi-port control valve and the reservoir to a sensor holder, according to embodiments of the invention.

DETAILED DESCRIPTION

Embodiments of the invention may relate to a multi-port control valve with multi-lumen paths diverging flow so that, the multi-port control valve fills and expels fluid at the same time through the same port for use in a blood sampling, blood pressure monitoring system that includes a sampling site, a pressure transducer, and reservoir. The multi-port control valve may include a rotatable valve member and three ports. Each of the three ports is connected to one of the sampling site, the pressure transducer, and the reservoir. In particular, the rotatable valve member is rotatable, such that, depending upon a position of the rotatable valve member, one of the three ports may be blocked from fluid communication with the other two ports. The modes of operation may comprise: a flushing/priming mode, a monitoring mode, a drawing/re-infusing mode, and a sampling mode. As will be described in more detail hereafter, the multi-port control valve and the reservoir include a unique structure comprising various fluid flow dividers and directors in the multi-port control valve and the reservoir that provide for a complete flushing of residual blood from the reservoir during the flush operation.

Figure 1:
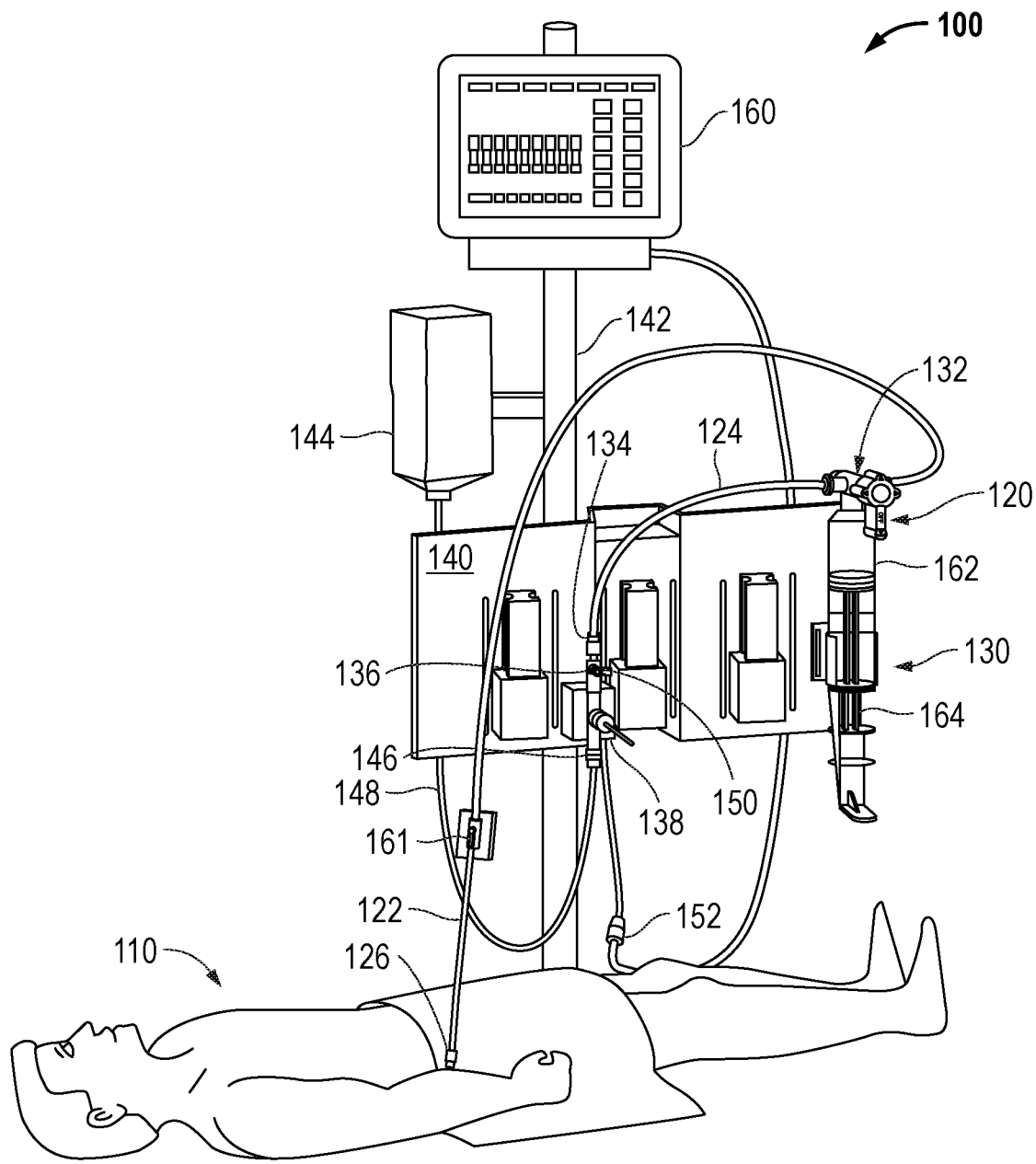
FIG. 1 is a diagram illustrating an example blood sampling system in an example blood sampling, blood pressure monitoring system as may be set up in a hospital room and connected to a patient.

As an example, a clinician may rotate the rotatable valve member through a valve handle that is connected thereto. The valve handle may have a visual indicator on it that is visually indicative of one of the plurality of modes of operation (e.g., a flushing/priming, mode, a monitoring mode, a drawing/re-infusing mode, and a sampling mode). Therefore, a system and method for indicating to the clinician, in an intuitive manner, the present mode of operation based upon rotating the valve handle, as well as, for assisting the clinician in correctly turning the rotating valve handle to the next desired position (which corresponds to the next desired mode of operation) is provided. Various examples of these implementations will be hereafter described in more detail FIG. 1 illustrates an example blood sampling system 120 in an example blood sampling, blood pressure monitoring system 100 as may be set up in a hospital room and connected to a patient 110. The blood sampling system 120 comprises a conduit line having a distal segment 122 toward the patient 110 and a proximal segment 124. The conduit line is primarily medical grade pressure tubing. The distal segment 122 may terminate in a male luer connector 126 for attaching to a female luer connector (not shown) of an injection site, or other conduit leading to the patient 110. A reservoir 130 connects to the conduit line via a multi-port control valve 132 interposed between the distal segment 122 and the proximal segment 124. The multi-port control valve 132 externally resembles a stopcock and controls fluid flow between the conduit line and the reservoir 130.

The proximal segment 124 extends from the multi-port control valve 132 and terminates in a female luer connector 134 attached to a stopcock 136 of a pressure transducer 138 (e.g., a disposable pressure transducer (DPT)). The reservoir 130 and pressure transducer 138 removably mount to a bracket 140 which, in turn, may be secured to a conventional pole support 142 with the reservoir 130 in a vertical orientation.

As mentioned above, the blood sampling system 120 forms a portion of the blood sampling, blood pressure monitoring system 100, and the pressure transducer 138 may be a DPT. However, it should be appreciated that any type of pressure monitoring device may be utilized.

A supply of flush solution 144 connects to a flush port 146 of the transducer 138 via tubing 148. Typically, the flush solution 144 comprises a bag of physiological fluid such as saline surrounded by a pressurized sleeve that squeezes the fluid and forces it through the tubing 148. In addition, an infusion fluid supply (not shown) may be provided in communication with an infusion port 150 of the stopcock 136. The pressure transducer 138 is thus placed in fluid communication with the arterial or venous system of the patient 110 through the conduit line, and includes a cable and plug 152 to connect to a suitable display monitor (e.g., patient monitor 160). The pressure transducer 138 is shown positioned within the proximal segment 124.

A fluid sampling site 161 that includes a Z-shaped flow passage adjacent a pre-slit septum may be utilized to sample blood. The septum preferably comprises an elastomeric disc which accepts a blunt cannula and reseals after each sample is drawn, reducing the potential for contamination and eliminating the danger of needle sticks. However, any type of fluid sampling site may be utilized.

The blood sampling reservoir 130 may include a syringe-type variable volume chamber 162, though other reservoirs that have constant volume chambers or other receptacles for receiving fluid may be used. The reservoir 130 is of a type that includes a channel through the variable volume chamber 162 for passage of flushing fluid there through.

In one mode of operation of the sampling system 120, a reduced pressure is created within the variable volume chamber 162 by withdrawing the plunger 164 such that a fluid sample from the distal segment 122 is drawn into the chamber 162. The chamber 162 may have a sufficient volume, e.g., 12 ml, to draw blood from the patient 110 past the sampling site 161. The clinician can then take a sample of undiluted blood from the sampling site 161. Subsequently, the blood and other fluids drawn into the reservoir 130 during the sampling operation are re-infused by depressing the plunger 164. It should be noted that the pressure transducer 138 may include a flow restrictor or flow control means to prevent flushed solution from going proximally through the sensor rather than back to the patient 110. For instance, the stopcock 136 may be used to close off the fluid path through the pressure transducer 138 prior to re-infusing the reservoir clearance volume.

The entire sampling system 120 is thus closed as the "priming" volume that ensures a pure sample of blood reaches the sampling site 161 remains within the sampling system 120 and is reinfused into the patient.

With additional reference to FIGS. 2A-2B, an example of the multi-port control valve 132 of the sampling system 120, will be described. As has been described, the multi-port control valve 132 for use in the blood sampling, blood pressure monitoring system 100 that includes a sampling site 161, a pressure transducer 138, and a reservoir 130, may include a rotatable valve 170 and three ports 172, 174, and 176. Port 172 may be connected to appropriate tubing to the sampling site 161. Port 174 may be connected to appropriate tubing to the pressure transducer 138. Port 176 may be connected to the reservoir 130.

As can be particularly seen in FIG. 2B, rotatable valve member 170 may be approximately cylindrical-shaped on top—with a rectangular divider below, and may be rotated around, such that, as will be described in more detail hereafter, depending upon a position of the rotatable valve member 170, one of the three ports 172, 174, and 176 may be blocked by the cylindrical-shaped surface of the rotatable valve member 170 from fluid communication with the other two ports. Further, port 176 may have a divider 178 that divides fluid flow to and from the reservoir 130 below. As will be described in more detail hereafter, the port from the multi-port control valve 132 that connects to the reservoir 130 includes a unique structure comprising a fluid flow divider 178 in the multi-port control valve (e.g., with rotatable valve member 170) that interacts with a fluid flow director of reservoir 162 that provides for a complete flushing of residual blood from the reservoir during the flush operation.

Figure 2A:
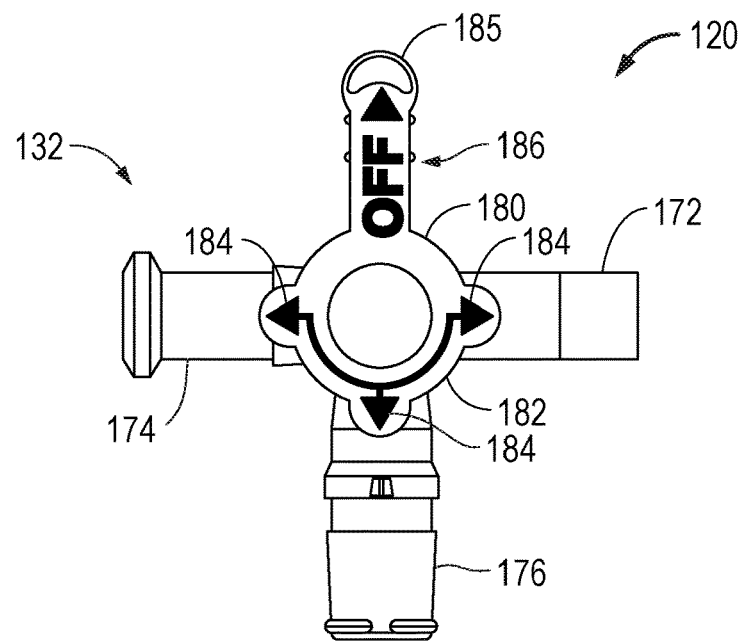
FIGS. 2A-2B are diagrams illustrating a front view and a cross-section view of an example of a multi-port control valve, according to embodiments of the invention.
Figure 2B:
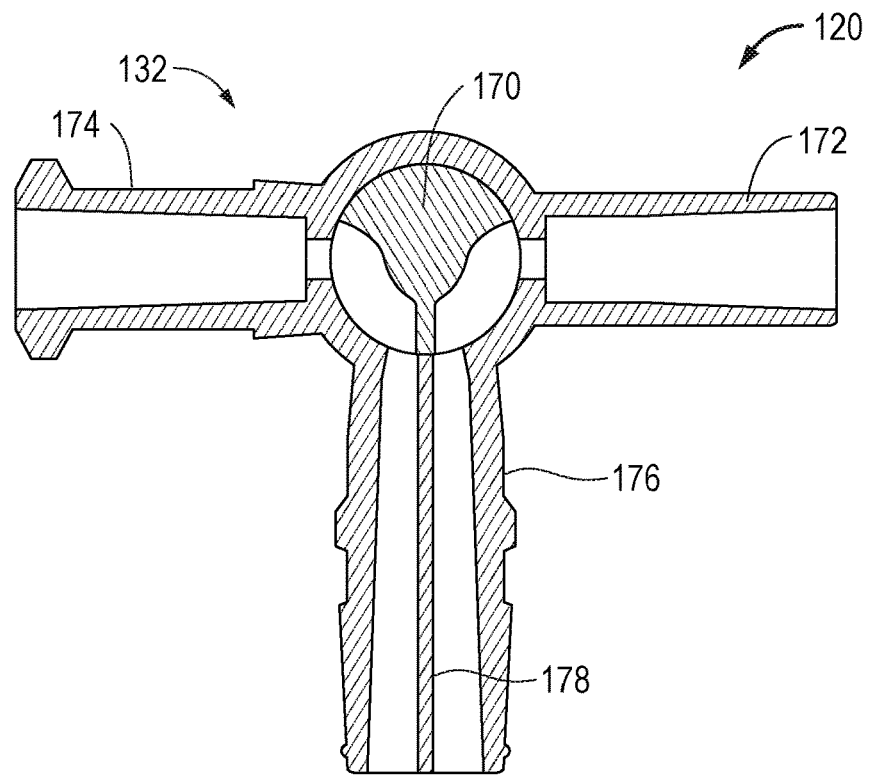

As can be seen in FIGS. 2A and 2B, a visual indicator that is visually indicative of one of the plurality of modes of operation controlled by the control valve 132, based upon the position of the rotatable valve member 170, is shown. In one embodiment, this visual indicator may be shown on a valve handle 180 that is connected to the rotatable valve member 170. In particular, the valve handle 180 may be coupled to the rotatable valve member 170 such that the rotatable valve member 170 rotates in synchrony with the valve handle 180. It should be appreciated that valve handle 180 may be connected to rotatable valve member 170 by any suitable connection means or the valve handle 180 and rotatable valve member 170 may be one singular component.

The valve handle 180 may show a visual indicator indicative of the mode of operation (e.g., a flushing/priming mode, a monitoring mode, a drawing/re-infusing mode, and a sampling mode), as will be described in more detail hereafter. The valve handle 180 may have a centered circular portion 182, a plurality of arrows 184 extending from the circular portion that are used to align with ports, and a long rectangular handle member 185 that is actuated by a clinician for rotation. In particular, the handle 185 has an OFF indicator 186 (with an arrow) that is used to select and indicate the mode of operation (e.g., a flushing/priming mode, a monitoring mode, a drawing/re-infusing mode, and a sampling mode), as will be described in more detail hereafter. Therefore, the OFF visual indicator 186 on the handle 185 can be used by the clinician to choose the mode of operation. Also, the plurality of arrows 184 align with the ports. It should be noted that, when the OFF indicator 186 is particularly positioned with a port, this is an indication that that port is closed by the rotatable valve member 170.

As examples, when the OFF indicator 186 of the handle 185 is pointed to the reservoir port 176, this indicates that the blood pressure monitoring mode is activated and that the reservoir port 176 is blocked from fluid communication with the other two ports 172 and 174. When the OFF indicator 186 of the handle 185 is pointed to the pressure transducer port 174, this indicates that a drawing/re-infusing mode is activated and that the pressure transducer port 174 is blocked from fluid communication with the other two ports 172 and 176. When the OFF indicator 186 of the handle 185 is pointed to the sampling port 172, this indicates a sampling mode is activated and that the sampling site port 172 is blocked from fluid communication with the other two ports 174 and 176. Further, when the OFF indicator 186 of the handle 185 is pointed up, this indicates a flushing/priming mode and all of the ports 172, 174, and 176 are all open for fluid communication.

As an example, a clinician may rotate handle 185 of valve handle 180 that is connected to rotatable valve member 170 to select a desired operational mode. In particular, the OFF indicator 186 of handle 185 provides a visual indicator that is visually indicative of the desired mode of operation (e.g., a flushing/priming mode, a monitoring mode, a drawing/re-infusing mode, and a sampling mode), as will be described in more detail hereafter. Further, the arrows 184 align with ports to further indicate the correct positioning and mode. Therefore, a system and method is provided for indicating to the clinician, in an intuitive manner, the present mode of operation based on rotating the handle 185 of the valve handle 180 that is very useful in assisting the clinician in correctly turning the rotating valve handle 180 to a next desired position, which corresponds to the next desired mode of operation. Various examples of these implementations will be hereafter described in more detail.

With additional reference to FIGS. 3A-3D and 4A-4D, various modes of operation will be described. Looking at these figures, it should be appreciated that pressure transducer port 174 connects to appropriate tubing to support fluid flow to pressure transducer 138; sampling port 172 connects to appropriate tubing to support fluid flow to sampling site 161; and reservoir port 176 is connected to reservoir 130, as previously described.

As has been previously described, when handle 185 is rotated to a desired position for a desired operational mode (e.g., a flushing/priming mode, a monitoring mode, a drawing/re-infusing mode, and a sampling mode), rotatable valve member 170 is rotated to the proper position to block fluid flow from any one of the three ports 172, 174, 176 with fluid flow communication with the other two ports, or may allow fluid flow communication between all three ports 172, 174, and 176 (e.g., flushing/priming mode). When a port of the control valve 132 is blocked by the rotatable valve member 170 from fluid communication with the other two ports, it can be referred to as being closed; otherwise, it can be referred to as being open.

Figure 5A:
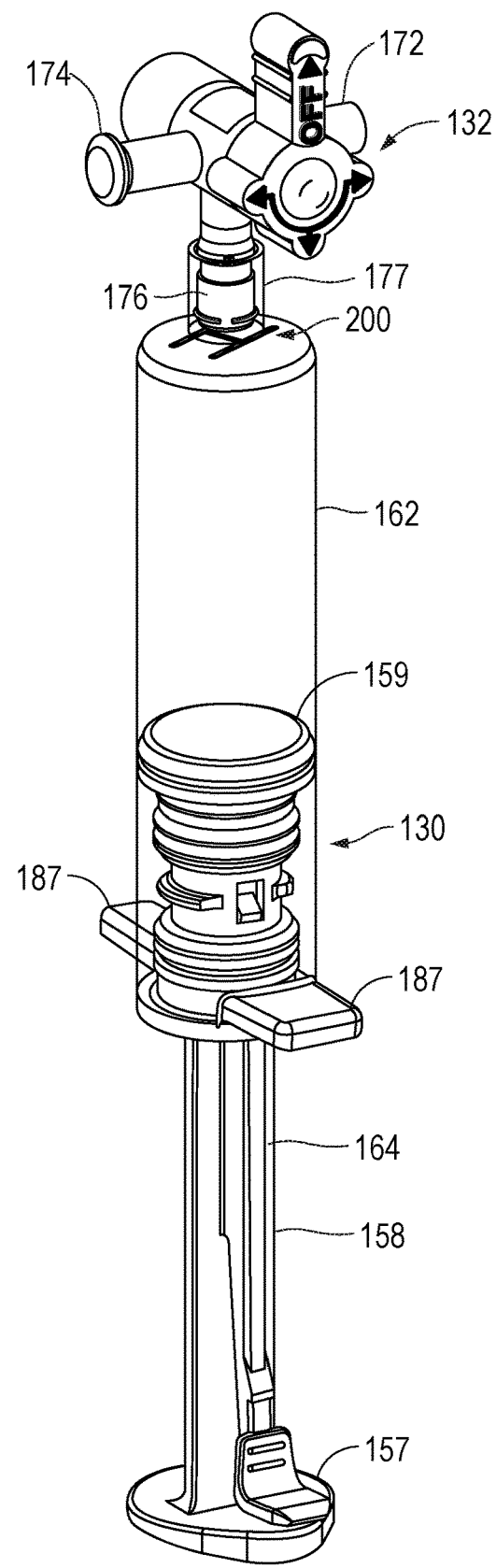
FIGS. 5A-5D are diagrams illustrating various perspective, cross-section, and other views of the multi-port control valve and a reservoir, according to embodiments of the invention.
Figure 5B:
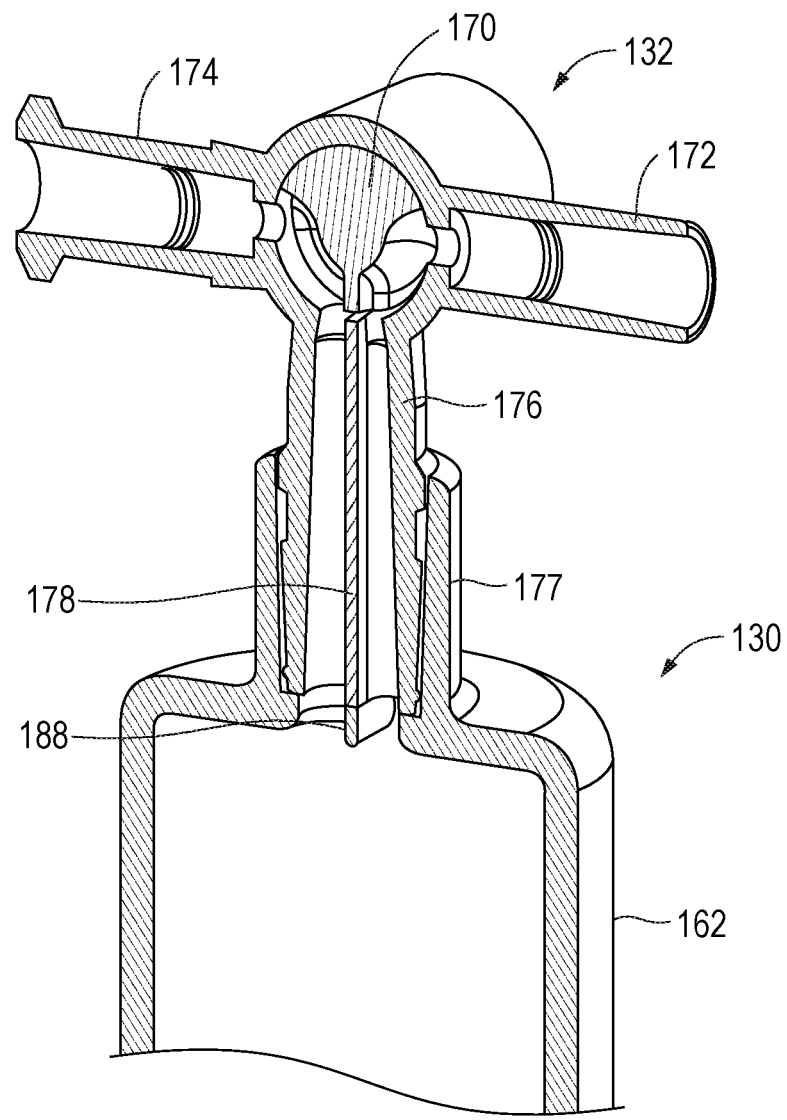

With brief additional reference to FIGS. 5A and 5B, as has been described, the multi-port control valve 132 may be connected to the blood sampling reservoir 130. The blood sampling reservoir 130 may include a syringe-type variable volume chamber 162. In particular, the reservoir port 176 may connect within an approximately circular receiving portion 177 of the chamber 162. As has been described, a reduced pressure is created within the chamber 162 by withdrawing the plunger 164 (e.g., having a push/pull handle 157, a rod 158, and a head 159) such that a fluid sample is drawn into the chamber 162. The chamber 162 may have a sufficient volume, e.g., 12 ml, to draw blood from the patient 110 past the sampling site 161. The clinician can then take a sample of undiluted blood from the sampling site 161. Subsequently, the blood and other fluids drawn into the reservoir 130 during the sampling operation are re-infused by depressing the plunger 164. Also, the volume chamber 162 may have a pair of protruding rectangular sections 187. As will be described, and as shown in FIG. 5B, by utilizing a divider 178 in the reservoir port 176 of the multi-port control valve 132 that mates with a divider 188 in the chamber 162 of the reservoir 130, a fluid circuit is created from multi-port control valve 132 through the reservoir 130 and back to the multi-port control valve 132. As will be described, by utilizing the divider 178 in the reservoir port 176 of the multi-port control valve 132 that mates with the divider 188 in the volume chamber 162, a complete flushing of residual blood from the reservoir may be achieved.

With particular reference again to FIGS. 3A and 4A, the clinician may rotate handle 185 to the top position as shown in FIGS. 3A and 4A such that the OFF indicator 186 is pointed upwards. This corresponds to the flushing/priming mode of operation, meaning that all fluid communications are open. In particular, when the OFF indicator 186 of the handle 185 is pointed up, the rotatable valve member 170 is pointed up, such that all of the ports: sample site port 172, pressure transducer port 174, and reservoir port 176; are all open for fluid communication. During the flushing/priming mode of operation, the reservoir 130, sample sites 161, and tubes can be flushed, cleared, and de-bubbled. Also, a snap tab of the pressure transducer 138 may be pulled to flush saline and clear air bubbles. In this mode of operation, portions of the blood sampling, blood pressure monitoring system 100 may be cleared for operation.

Figure 4A:
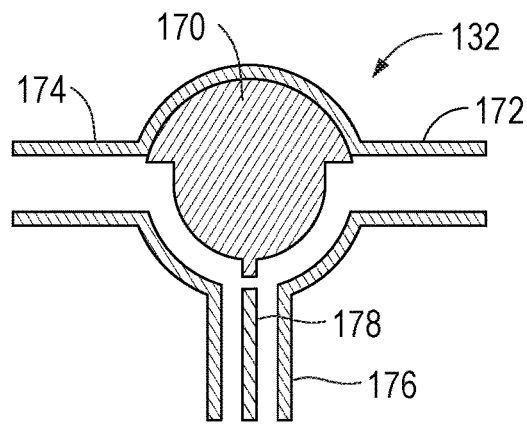
FIGS. 4A-4D are diagrams illustrating cross-section views of the multi-port control valve in various modes of operation, according to embodiments of the invention.
Figure 4B:
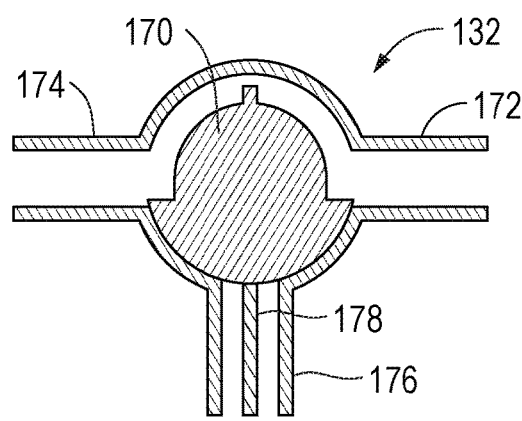

With reference to FIGS. 3B and 4B, when blood pressure monitoring is desirable by the blood pressure transducer 138, the clinician may rotate handle 185 to another position, which corresponds to the blood pressure monitoring mode. In this position, when the OFF indicator 186 of the handle 185 is pointed downward to the reservoir port 176, this indicates that the blood pressure monitoring mode is activated. In this position, the rotatable valve member 170 blocks fluid communication from the reservoir port 176 with the pressure transducer port 174 and the sampling site port 172 such that fluid communication from the reservoir 130 is blocked from the pressure transducer 138 and sampling site 161. In this way, the reservoir 130 is closed from fluid communication to isolate the reservoir 130 from the blood pressure monitoring system so that it does not interfere with blood pressure measurement. In particular, in this configuration, there is a direct high fidelity fluid link between the patient 110 through the tubes to pressure transducer 138 for blood pressure measurement.

Figure 4C:
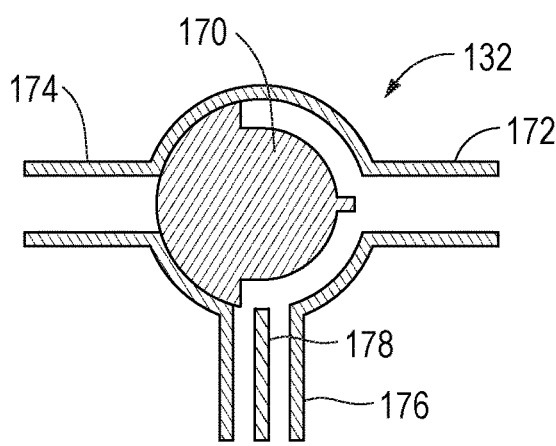

When the clinician would like a blood sample, the clinician should engage in a drawing/re-infusing mode operation. With reference to FIGS. 3C and 4C, the clinician may rotate handle 185 to another position, which corresponds to the drawing/re-infusing mode. In this position, when the OFF indicator 186 of the handle is pointed to the pressure transducer port 174, this indicates the drawing/re-infusing mode is activated. In this position, the rotatable valve member 170 blocks fluid communication from the pressure transducer port 174 with the reservoir port 176 and sampling site port 172 such that fluid communication from pressure transducer 138 is blocked from the reservoir 130 and the sampling site 161. In this way, in the drawing/re-infusing mode operation, a clearing volume can be pulled from the distal segment of the patient 110 through the tube by pulling plunger 164 of the reservoir 130 downward such that a mixture of blood and saline is pulled by the plunger 164 into the chamber 162 of the reservoir 130. Based upon this, a sampling mode can be initiated.

Figure 4D:
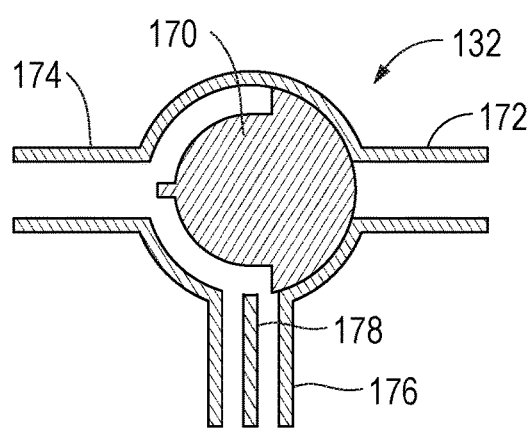

Next, when the clinician wishes to obtain a blood sample, the clinician should engage in a sampling mode operation. With reference to FIGS. 3D and 4D, the clinician may rotate handle 185 to another position, which corresponds to the sampling mode. In this position, when the OFF indicator 186 of the handle is pointed to the sampling port 172, this indicates the sampling mode is activated. In this position, the rotatable valve member 170 blocks fluid communication from the sampling port 172 with the reservoir port 176 and pressure transducer port 174 such that fluid communication from sampling site 161 is blocked from the reservoir 130 and the pressure transducer 138. In this way, in the sample mode operation, fluid may be drawn from the sampling site 161 that comes purely from the patient 110 and not from the reservoir 130 or other areas (e.g., such as, the pressure transducer 138). Thus, blood can be withdrawn from the sampling site 161 with pure blood in a secure manner, as previously described.

Continuing with these modes of operation, once the blood sample is drawn, the clinician may rotate handle 185 to the drawing/re-infusing mode position (FIGS. 3C and 4C). In this position, when the OFF indicator 186 of the handle is pointed to the pressure transducer port 174, this indicates the drawing/re-infusing mode is activated, as previously described. In this position, the rotatable valve member 170 blocks fluid communication from the pressure transducer port 174 with the reservoir port 176 and sampling site port 172 such that fluid communication from pressure transducer 138 is blocked from the reservoir 130 and the sampling site 161. In the drawing/re-infusing mode operation (e.g., with additional reference to FIG. 1), the plunger 164 may be pushed up by the clinician at a slow rate until the plunger 164 latches onto the closed and locked position of the reservoir 130 such that the clearing volume (e.g., saline and blood mixture) is pushed back through the appropriate tubing back to the patient 110. Next, the clinician may rotate handle 185 to the top position (FIGS. 3A and 4A), such that the OFF indicator 186 is pointed upwards to the flushing/priming mode operation such that all fluid communications are open. During the flushing/priming mode operation, the reservoir 130, sample sites 161, and tubes can be flushed, cleared, and de-bubbled. Also, a snap tab of the pressure transducer 138 may be pulled to flush saline and clear air bubbles. In this mode of operation, portions of the blood sampling, blood pressure monitoring system 100 may be cleared for operation.

With particular reference to FIGS. 5A-5D, structural features of the multi-port control valve 132 and the reservoir 130 will be described that provide for the complete flushing of residual blood from the top part of the chamber 162 of the reservoir 130 when the head 159 of the plunger 164 latches onto the closed and locked position of the reservoir 130 after the re-infusing mode operation and when the flush mode operation has been engaged in. In particular, by utilizing a divider 178 in the reservoir port 176 of the multi-port control valve 132 that mates with a divider 188 in the volume chamber 162 of the reservoir 130, a fluid circuit is created from the multi-port control valve 132 through the reservoir 130 and back to the multi-port control valve 132. By utilizing the divider 178 in the reservoir port 176 of the multi-port control valve 132 that mates with the divider 188 in the volume chamber 162, in combination with a fluid director 200 (as will be described) attached to divider 188, a complete flushing of residual blood from the area between the head 159 of the plunger 164 and the area of the chamber 162 (i.e., the top area 202 and the outside circumference 204 of the chamber 162), and the head 159 itself, may be achieved during the flush operation. As an example, there may only be a 0.01 inch height between the head 159 of the plunger 164 and the top area 202 of the chamber 162. In one example, the fluid director 200 may be approximately H-shaped having two opposed bars 210 and 212. However, this is only one example shape of a fluid director and any suitable shape to guide fluid to clean the interior of the chamber 162 may be used (e.g., Y-shapes, W-shapes, etc.)

Figure 5C:
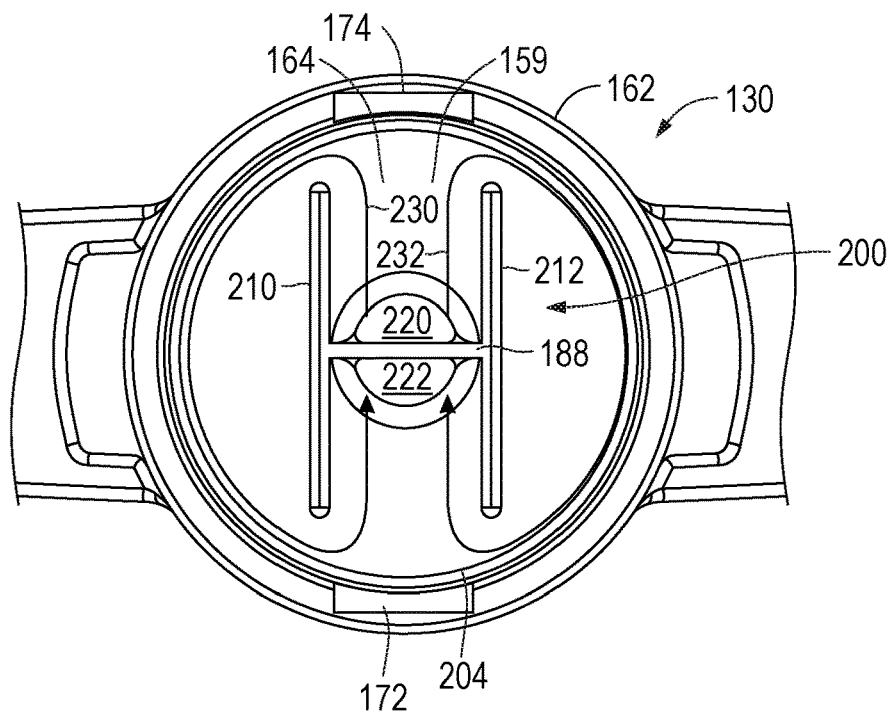
Figure 5D:
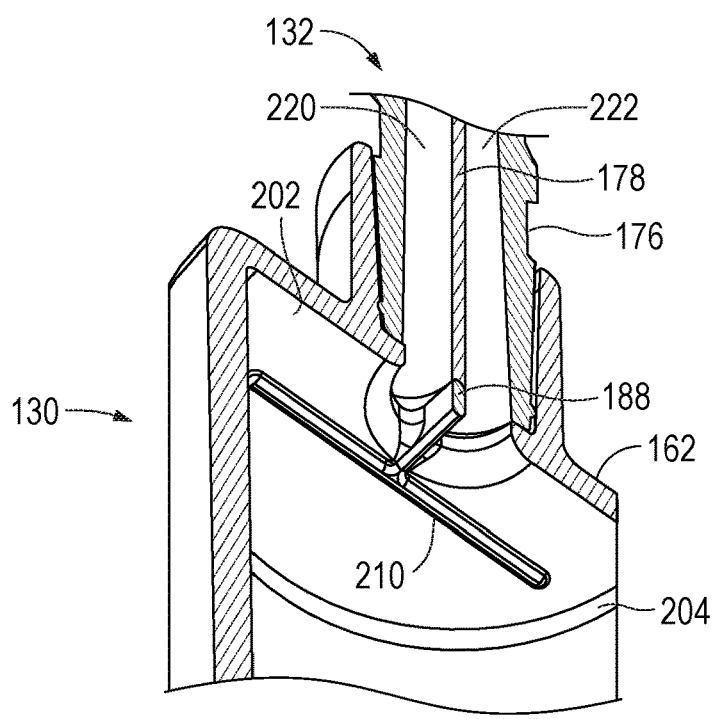

With particular reference to FIGS. 5C and 5D, during a flush mode operation, saline is flushed through the pressure transducer port 174 down first channel 220 divided by dividers 178 and 188 such that the saline flows against the head 159 of the plunger 164 and is guided by the opposed bars 210 and 212 of the H-shaped fluid director 200 against the outside circumference 204 and the top area 202 of the chamber 162 around the inside of the chamber (e.g., following lines 230 and 232) such that the fluid is then flushed out of the chamber up second channel 222 divided by dividers 178 and 188 through the sampling site port 172 back to the tubing and the patient. In the flush operation, the reservoir 130, sample sites 161, and tubes can be flushed, cleared, and de-bubbled. However, by the particularly described structure, a sufficient, suitable, adequate, or complete flushing of residual blood from the area between the head 159 of the plunger 164 and the area of the chamber 162

(i.e., the top area 202 and the outside circumference 204 of the chamber 162), and the head 159 itself, may be achieved during the flush operation.

With reference again to FIGS. 3A-3D and 4A-4D, next the clinician may again enable blood pressure monitoring mode by rotating handle 185 back the blood pressure monitoring position, in which, the OFF indicator 186 of the handle 185 is pointed downward to the reservoir port 176 (FIGS. 3B and 4B). As has been described, in the blood pressure monitoring mode, the reservoir port 176 towards the reservoir 130 is closed from fluid communication to isolate the reservoir 130 from the blood pressure monitoring system so that it does not interfere with blood pressure measurement. In particular, in this configuration, there is a direct high fidelity fluid link between the patient 110 through the tubes to pressure transducer 138 for blood pressure measurement.

As has been described, all of the modes of operation (e.g., a flushing/priming mode, a monitoring mode, a drawing/re-infusing mode, and a sampling mode) may be activated by a clinician in a very straight forward manner by rotating handle 185 such that the OFF indicator 186 is in an appropriate position to inform the clinician as to what mode of operation the blood sampling, blood pressure monitoring system 100 is operating in. Also, it should be appreciated that because the pressure transducer 138 contains a small orifice in the normal state, fluid flow is restricted, such that, although all fluid communications are open when the valve member 170 is in the flushing position, all the fluid flow pulled into the reservoir 130 should come from the patient side. Because of this, the flushing/priming mode may be used in some instances, instead of the drawing/re-infusing mode.

As has been described, a clinician may rotate handle 185 of valve handle 180 that is connected to rotatable valve member 170 to select a desired operational mode. In particular, the OFF indicator 186 of handle 185 provides a visual indicator that is visually indicative of the desired mode of operation (e.g., a flushing/priming mode, a monitoring mode, a drawing/re-infusing mode, and a sampling mode). Further, the arrows 184 align with ports to further indicate the correct positioning and mode. Thus, a system and method is provided for indicating to the clinician, in an intuitive manner, the present mode of operation based on rotating the handle 185 of the valve handle 180 that is very useful in assisting the clinician in correctly turning the rotating valve handle 180 to a next desired position, which corresponds to the next desired mode of operation. With the assistance of the visual indication assembly, confusion as to the present mode of operation of the control valve and to the correct way to rotate the valve member/handle for the next desired mode of operation may be reduced, and the work efficiency of the clinician improved.

It should be noted that the OFF indicator 186 with the arrow indicates that the blocking member of the rotatable valve member 170 is present and that the port (if one is present) is closed. However, the other arrows 184 indicate that the ports are open (i.e., the rotatable valve member is not blocking fluid) and further that the lines 187 between the arrows 184 indicate an open fluid path. Therefore, each of the previously described modes of operation (the flushing/priming mode, the monitoring mode, the drawing/re-infusing mode, and the sampling mode), that are easily selectable by the clinician, via the OFF indicator 186, the arrows 184, and the lines 187, indicate what port is closed (OFF indicator 186), what ports are open (arrows 184), and the directions of the fluid flow (lines 187).

As previously described examples, when the OFF indicator 186 of the handle 185 is pointed to the reservoir port 176, this indicates that the blood pressure monitoring mode is activated and that the reservoir port 176 is blocked from fluid communication with the other two ports 172 and 174, and that the sampling port 172 and the pressure transducer port 174 are open (arrows 184 point to them), and fluid flows between the ports as indicated by the lines 187 and arrows 184 (FIG. 3B). When the OFF indicator 186 of the handle 185 is pointed to the pressure transducer port 174, this indicates that a drawing/re-infusing mode is activated and that the pressure transducer port 174 is blocked from fluid communication with the other two ports 172 and 176, and that the sampling port 172 and the reservoir port 176 are open (arrows 184 point to them), and fluid flows between the ports as indicated by the lines 187 and arrows 184 (FIG. 3C). When the OFF indicator 186 of the handle 185 is pointed to the sampling port 172, this indicates a sampling mode is activated and that the sampling site port 172 is blocked from fluid communication with the other two ports 174 and 176, and that the pressure transducer port 172 and the reservoir port 176 are open (arrows 184 point to them), and fluid flows between the ports as indicated by the lines 187 and arrows 184 (FIG. 3D). Further, when the OFF indicator 186 of the handle 185 is pointed up, this indicates a flushing/priming mode and all of the ports (pressure transducer port 174, reservoir port 176, and sampling site port 172) are open (arrows 184 point to them) for fluid communication, and fluid flows between the ports as indicated by the lines 187 and arrows 184 (FIG. 3A).

As can be particularly seen in FIGS. 3A-3D, particular implementations of the arrows 184, lines 187, and OFF indicators 186, will now be described. As has been described, the arrows 184, lines 187, and OFF indicators 186 are put on the three-port control valve 132 that are different than typical stopcock valves and provide a clear indication of the fluid path directions and what operational mode the multi-port control valve 132 is in. As can be seen in FIGS. 3A-3D, the indicators (the arrows 184, the lines 187, the OFF indicator 186) may be slightly raised or elevated relative to the rest of the rotatable handle 185. As one example, the indicators (the arrows 184, the lines 187, the OFF indicator 186) may be molded into the handle (e.g., embossed), and hot foil stamped directly on the raised surface to provide contrast (e.g., color) from the rotatable handle 185. As one example, the rotatable handle may be white and the color of the indicators (the arrows 184, the lines 187, the OFF indicator 186) may be black. However, any suitable colors may be utilized.

Also, in one implementation, the top of the multi-port control valve 132 may have a rectangular visual indicator 195 and the top of the rotatable handle may have a pair of aligned rectangular lines 197. When, the multi-port control valve 132 and the system are in the blood pressure monitoring mode, FIG. 3B, the alignment of the pair of aligned rectangular lines 197 with the rectangular visual indicator 195 (along with the OFF indicator 186 pointing down), provides a very clear indicator to the clinician that the system is set for the blood pressure monitoring mode. In some examples, the pair of aligned rectangular lines 197 and the rectangular visual indicator 195 may be colored (e.g., green, red, yellow, any color) for further visual indication to the clinician. The colors of the rectangular lines and the rectangular visual indicator may be the same colors or different colors. Further, any sort distinguishing color, shape, design, etc., may be used to increase the visual indication to the clinician. Also, in one example, the top and bottom of the rotatable hand 185 may include aligned raised rectangular lines 199 to provide indicators and grabbing ease to the clinician's fingers to rotate the rotatable handle.

It should be appreciated that although various visual indicator types (e.g., arrows, terminology (e.g., OFF), handles, structures, etc.) to indicate the various operational modes have been described in detail, that these are just examples, and that any suitable visual indicator type may be utilized to inform the clinician of the operational mode of the blood sampling, blood pressure monitoring system 100.

It should be appreciated that previously described design structures allow for the use of the multi-port control valve 132 to allow for the isolation of the reservoir 130 during blood pressure monitoring that enhances the frequency response of the blood pressure monitoring device, which further allows for the increase of working length (e.g., increased working length tubing). In particular, the isolation of the reservoir maintains a high fidelity of the frequency response—allowing for the longer working tubing length. The increased working length may be useful for use in the operating room. Further, the previously described design structures allow for the flushing of all unwanted blood from the reservoir 130 during flushing.

Figure 6A:
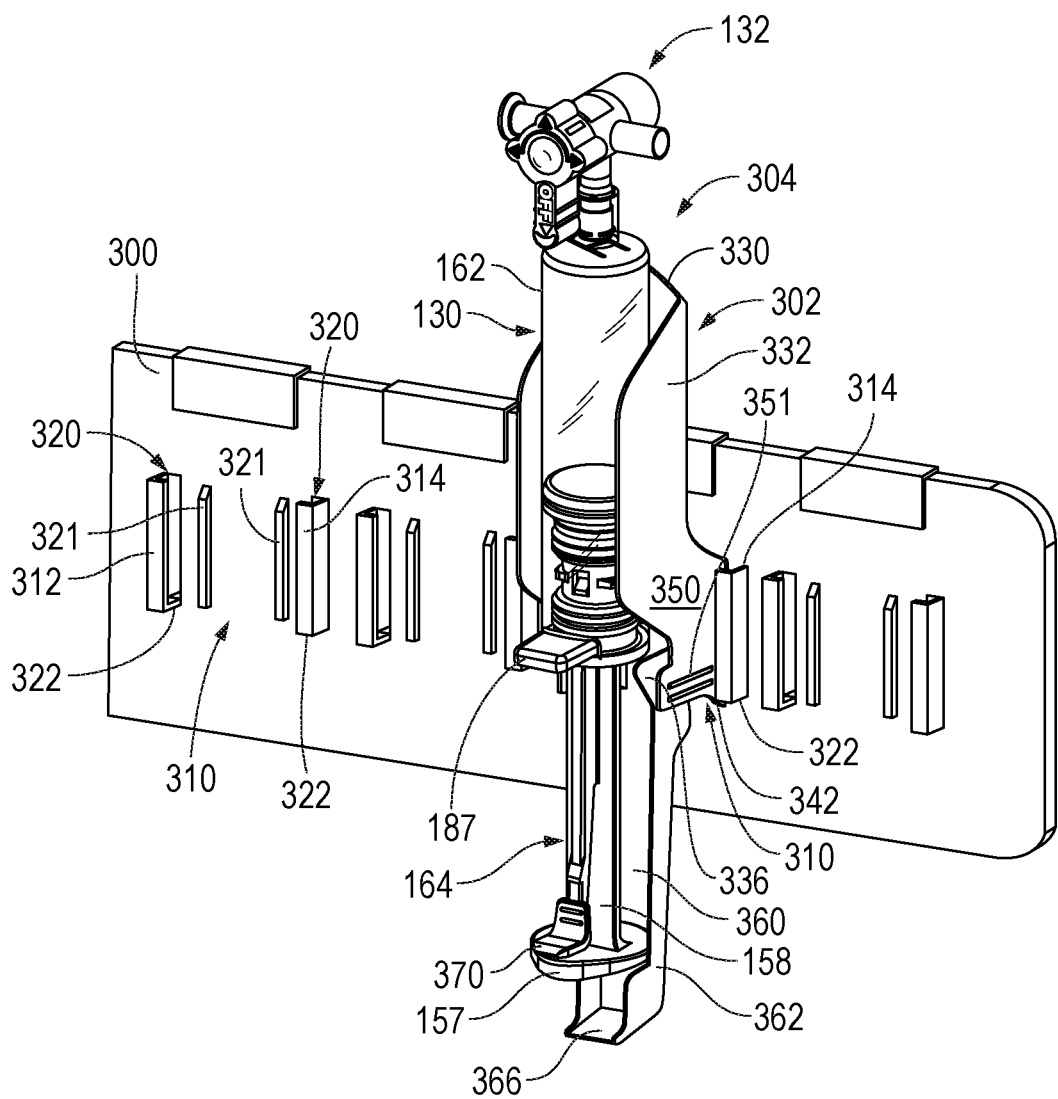

With reference to FIGS. 6A-6C, as will be described, the multi-port control valve 132 and the reservoir 130 (e.g., the device 304) may be mounted to a sensor holder 300 with a bracket 302 having a clip that automatically engages the sensor holder 300 upon installation. When the clinician intends to remove the device 304, the clinician simply needs to disengage the clip in order to remove the device 304 from the sensor holder 300. The bracket 302 with the clip, as will be described, holds the device 304 in a fixed manner to avoid movement and falling—while allowing easy mounting and demounting by a clinician without discomfort to the clinician.

In particular, with reference to FIGS. 6A-6C, the bracket 302 for mounting the multi-port control valve 132 and the reservoir 130 (e.g., the device 304) to the sensor holder 300 will be more particularly described hereafter. Looking at the sensor holder 300, the sensor holder 300 may be approximately rectangular shaped and may be mountable to an IV pole—as sensor holders typically are (e.g., see FIG. 1). In particular, sensor holder 300 may include a plurality of mounting sections 310 that include two-opposed rectangular portions 312 and 314 that each have slots 320 and bottoms 322. As will be described, the slots 320 and bottoms 322 may receive flanges of the bracket 302 and clips. Also, the mounting sections 320 may include guide rails 321 that may be used by devices.

Looking particularly at the bracket 302, the bracket 302 may include a curved backside 330 and two extending sidewalls 332 with curved portions that extend therefrom to surround, hold, and mount the chamber 162 of the reservoir 130 therein. Further, extending downward with the two extending sidewalls 332 with curved portions are engagement areas 350 having two indicator lines 351. Also, bracket 302 may include a base table 336 to abut the bottom of the reservoir including one of the protruding rectangular sections 187 to hold the reservoir in place. Furthermore, the backside 330 may include an approximately rectangular opening 331 to accept one of the protruding rectangular sections 187 mounted against the base table 336 for further mounting stability. Moreover, bracket 302 may include a pair of one-way clips 342 that clip into place when the bracket 302 is mounted into a mounting section 310 of the sensor holder 300 by a clinician, as will be described. The clips 342 extend as flanges from the engagement areas 350. Additional flanges 340 extend from the sidewalls 332 and the engagement areas 350, respectively.

Also, bracket 302 may include a downward extending plunger section 360 with sidewalls 362 and a base portion 366 that tapers downward from the base table 336. The plunger section 360 may be used to partially cover and protect the push-pull handle 157 and rod 158 of the plunger 164. As can be seen in FIG. 6A, the push-pull handle 157 may also have an L-shaped thumb feature 370 including two rectangular indicators for easy pushing and pulling by the clinician. The base portion 366 may prevent the push-pull handle 157 from over extending.

In particular, when the bracket 302 firmly holding device 304 is mounted by the clinician to the sensor holder 300, the mounting sections 310 with the two opposed rectangular portions 312 and 314 having slots 320 and bottoms 322 receive the flanges 340 of the bracket 302 including the clips 342. When the bracket 302 is placed by the clinician in the mounting section 310, the flanges 340 of the bracket are received by the slots 320 and the flange's bottoms abut the bottoms 322 of the two opposed rectangular portions 312 and 314 and the clips 342 clip around the bottoms 322 of the two opposed rectangular portions 312 and 314, such that the bracket 302 is mounted in place with audible and visual cues. On the other hand, to remove the bracket 302, the clinician actuates the two engagement areas 350 (easily findable by the clinician by two indicator lines 351) to thereby deflects the clips 342 inward to allow for disengagement of the clips 342 from the mounting section 310 of the sensor holder 300. With the clips 342 deflected inward, the clips 342 are disengaged from the bottoms 322 of the two opposed rectangular portions 312 and 314, allowing the clinician to easily remove the bracket 302 and the device 304 by pulling the bracket 302 upwards and out of the mounting section 310 of the sensor holder 300. The clips 342 can be manually actuated to allow removal of the bracket from the sensor holder 300, in such manner that prevents obstruction of the clinicians hand upon removal from sensor holder 300.

With the previously described structure of the sensor holder 300 and bracket 302, the two one-way clips 342 may easily snap into place when the bracket 302 holding the device 304 is pushed into place by the clinician into the mounting section 310, such that, the clips snap around the bottoms of the opposed rectangular portions. On the other hand, when the clinician intends to remove the bracket 302 holding the device 304, the clinician simply actuates the clips 342 by deflecting the two engagement areas 350. In particular, this may be achieved by deflecting the two engagement areas 350 (easily findable by the clinician by two indicator lines 351) to allow for the disengagement of the clips 342 from the bottoms of the opposed rectangular portions, such that, the bracket 302 holding the device 304 is easily moveable in the reverse direction (e.g. opposite of installation) out of the mounting section 310. By utilizing this structure, the clinician does not experience obstacles in removing the bracket 302 holding the device 304, and it is easy to remove. Also, this structure enables easy one-handed mounting and removal of the bracket 302 and device 304 by the clinician. Further, when the bracket 302 is locked into place, the clips 342 are connected to the sensor holder 300 in a very secure manner, by the clips 342 wrapping around the bottom portions of the two opposed rectangular portions, such that the bracket 302 holding the device 304 is securely mounted. In this way, the bracket 312 and the device 304 are very limited as to movement in response to being bumped, manipulated, and are much less susceptible to falling.

It should further be appreciated that although various types of valves, ports, and various other mechanical structures and components have been described, that these are only examples, and other types of mechanical components may be utilized to perform the same or similar functions. It should further be appreciated that the previously described mechanical structures and components may be made of any material, such as: plastic, metal, rubber, polymer, polyvinyl chloride, or any suitable material.

The various illustrative logical blocks, processors, modules, and circuitry described in connection with the embodiments disclosed herein may be implemented or performed with a general purpose processor, a specialized processor, circuitry, a microcontroller, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor may be a microprocessor or any conventional processor, controller, microcontroller, circuitry, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module/firmware executed by a processor, or any combination thereof. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A bracket for mounting a multi-port control valve and a reservoir to a sensor holder for use in a blood sampling-blood pressure monitoring system by a clinician, the sensor holder comprising a mounting section including two opposed rectangular portions having slots and bottoms, the bracket comprising:
   extending circular portions to form an interior portion to surround and mount the reservoir;
   a base table to abut the bottom of the reservoir to hold the reservoir in place;
   a pair of clips that clip into place with the sensor holder when the bracket is mounted into the mounting section by the clinician; and
   flanges that slide within the slots of the two opposed rectangular portions and abut the bottoms of the two opposed rectangular portions.

2. The bracket of claim 1, wherein each of the clips of the bracket respectively clip around the adjacent bottom of the adjacent rectangular portion to mount the bracket to the sensor holder.

3. The bracket of claim 2, wherein the bracket further comprises an opposed pair of engagement areas, each engagement area being coupled to a clip.

4. The bracket of claim 3, wherein, to remove the bracket from the sensor holder, the clinician squeezes the two engagement areas to squeeze the clips inward to allow for disengagement of the clip from the sensor holder.

5. The bracket of claim 4, wherein, with the clips squeezed inward, the clips are disengaged from the bottoms of the two opposed rectangular portions allowing the clinician to move the bracket upwards and out of the mounting section of the sensor holder.

6. The bracket of claim 3, wherein, each of the opposed pair of engagement areas include one or more indicator lines to provide a physical and visual indication to the clinician to squeeze the clips.

7. A sensor holder system for mounting a multi-port control valve and a reservoir in a blood sampling-blood pressure monitoring system by a clinician, the sensor holder system comprising:
   a mounting section including two opposed rectangular portions having slots and bottoms;
   and a bracket comprising:
   extending circular portions to form an interior portion to surround and mount the reservoir;
   a base table to abut the bottom of the reservoir to hold the reservoir in place; and
   a pair of clips that clip into place with the mounting section when the bracket is mounted into the mounting section by the clinician.

8. The sensor holder system of claim 7, wherein the bracket further comprises flanges that slide within the slots of the two opposed rectangular portions and abut the bottoms of the two opposed rectangular portions.

9. The sensor holder system of claim 8, wherein each of the clips of the bracket respectively clip around the adjacent bottom of the adjacent rectangular portion to mount the bracket to the mounting section.

10. The sensor holder system of claim 9, wherein the bracket further comprises an opposed pair of engagement areas, each engagement area being coupled to a clip.

11. The sensor holder system of claim 10, wherein, to remove the bracket from the sensor holder system, the clinician squeezes the two engagement areas to squeeze the clips inward to allow for disengagement of the clip from the mounting section.

12. The sensor holder system of claim 11, wherein, with the clips squeezed inward, the clips are disengaged from the bottoms of the two opposed rectangular portions allowing the clinician to move the bracket upwards and out of the mounting section of the sensor holder system.

13. The sensor holder system of claim 10, wherein, each of the opposed pair of engagement areas include one or more indicator lines to provide a physical and visual indication to the clinician to squeeze the clips.

* * * * *